United States Patent [19]

Okada et al.

[11] Patent Number: 4,653,491

[45] Date of Patent: Mar. 31, 1987

[54] WATER CONTENT SENSING AND INFORMING SYSTEM FOR A DISPOSABLE DIAPER

[75] Inventors: Shigeru Okada; Katsutoshi Rokuta, both of Kochi, Japan

[73] Assignee: Nippon Kodoshi Corporation, Kochi, Japan

[21] Appl. No.: 743,748

[22] Filed: Jun. 12, 1985

[30] Foreign Application Priority Data

Jun. 20, 1984 [JP] Japan .................................. 59-128238
Jul. 11, 1984 [JP] Japan .................................. 59-143649

[51] Int. Cl.⁴ ........................ A61B 19/00; G08B 21/00
[52] U.S. Cl. .............................. 128/138 A; 200/61.04; 340/573; 340/604
[58] Field of Search ................... 128/138 A; 604/361; 340/573, 604; 200/61.04, 61.06, DIG. 40

[56] References Cited

U.S. PATENT DOCUMENTS

| | | | |
|---|---|---|---|
| 3,508,235 | 4/1970 | Baisden | 128/138 A X |
| 3,530,855 | 9/1970 | Balding | 128/138 A |
| 3,759,246 | 9/1973 | Flack et al. | 128/138 A X |
| 4,271,406 | 6/1981 | Wilson | 128/138 A X |
| 4,356,818 | 11/1982 | Macias et al. | 128/138 A |

*Primary Examiner*—Richard T. Stouffer
*Attorney, Agent, or Firm*—Shlesinger, Arkwright, Garvey & Fado

[57] ABSTRACT

Water content sensing and informing system for a disposable diaper consisting of water permeable inner sheet, water absorber, and water impermeable outer sheet, comprises at least one pair of metal layers, one surface of one layer being covered with an electric insulating layer, formed between the water impermeable outer sheet and the water absorber, a detector for detecting water content absorbed in the diaper, and an informing mechanism for informing the detected result. The pair of metal layers is isolated with constant distance to each other and extended in the longitudinal direction of the diaper. The pair of metal layers is formed in a thin layer by a lamination or vacuum evaporation of a metal leaf. The informing mechanism is selected from a visual, auditory, remote informing device using an oscillator and receiver, or combination of these.

19 Claims, 9 Drawing Figures

WATER CONTENT SENSING AND INFORMING SYSTEM FOR A DISPOSABLE DIAPER

BACKGROUND OF THE INVENTION

1. Field of the Invention

The present invention generally relates to a system for sensing and informing about the water content absorbed by a disposable diaper. In its particular aspects, the present invention relates to a water content sensing and informing system for a disposable diaper which provides convenience and comfort to the person who wears it, such as babies or bedridden and aged people. Another person can easily learn of the wet condition of the diaper and change it instantly without delay.

2. Description of the Prior Art

Recently, the number of aged people has been increasing owing to the progress of medical science. The number of bedridden people has tended to increase simultaneously. In nursing hospitals for such aged people, it is estimated that at leased 30 percent of the patients are bedridden. The treatment of excrement has been a serious problem for those caring for these patients. It is obvious that providing easy treatment, for at least urine, would lighten the distress and burden of the patients and the nursing personnel.

Conventionally, two methods have been commonly used for such urine treatment. One method involves a diaper treatment using a diaper or napkin to absorb the excreted urine. The other method involves continuous urine excretion treatment using a urethral catheter, such as a balloon catheter, which must always be connected to the patient.

The above mentioned diaper treatment will be discussed in detail as the present invention is related to that type of treatment. In hospitals or nursing homes, the changing of the diapers of the patients is fixed at certain intervals because the nurse has no way of knowing whether all of the patients have urinated. However, with this method, some of the patients may be left with a wet diaper for a long time, thereby causing discomfort and pain due to diaper rash, cooling, bed sores and the like.

In order to learn of the urination of such patients, a particular method of detecting the water content, as in urine, has been provided. The method of detecting the water content by means of changes in the electric conductivity of electrodes, such as of an electric wire installed in the diaper, is known. With this method, the urination can be detected, but it does not permit a determination of the degree of wetness of the diaper. Therefore, a water content sensing system for disposable diapers has been proposed in our prior invention (Japanese Patent Application for Utility Model No. 59-71558) which system is illustrated in FIG. 8 and FIG. 9.

In the prior art illustrations, FIGS. 8 and 9, a disposable diaper equipped with a water content sensing means is shown. The diaper comprises a water permeable inner sheet 1, a water absorber 2 and a water impermeable outer sheet 3. Further, both side ends 3a of the outer sheet 3 are bent over to cover the periphery of the absorber 2. Each bent section is pinched between a pair of metal layers 4, as shown in FIG. 9. Each metal layer 4 is connected to a lead wire 5. Because of this construction, the absorber 2 is pinched between the outer sheet 3 and the pair of metal layers 4 and thereby a capacitor is formed. The electrostatic capacity of this capacitor corresponds to the amount of the water absorbed by the absorber 2. The degree of wetness can be determined by monitoring the changes in the electrostatic capacity through the use of a well-known measuring device which is connected to the lead wires 5.

This capacitor-type water content sensing diaper provides comfort to the patients, as wet diapers can be changed by the nurse or nursing person who learns of the degree of wetness of the diaper through the detecting device. However, the capacitor formed by this type of structure frequently causes erroneous detection of the degree of wetness due to the deformation of the metal layers 4. The distance between the two metal layers 4 can be changed by their becoming broken, disconnected or twisted. This can result in the erroneous measurement of the electrostatic capacity because the electrostatic capacity is proportional to the area of the metal layers and the dielectric constant of the water absorber 2 and is inversely proportional to the distance between the two metal layers. The deformation of the metal layers 4 can easily occur due to the movement of the patients or babies or whoever is wearing the diaper. Erroneous measurement of degree of the wetness may be caused by fluctuations in the electrostatic capacity, as described above.

The detecting and informing device is connected to each diaper, so that a nurse or a nursing person has to go look at each informing device to determine the wetness of the patient's diaper.

3. Objects of the Invention

It is an object of the present invention to provide a water content sensing and informing system for a disposable diaper which can detect the degree of wetness of the disposable diaper without requiring checking by a nursing person.

Another object of the present invention is to provide a water content sensing and informing system for a disposable diaper which can transmit the detected information to a remote location.

SUMMARY OF THE INVENTION

To accomplish the beforementioned objects, the present invention of a water content sensing and informing system for a disposable diaper comprises the below outlined structure. The disposable diaper primarily consists of a water permeable inner sheet, a water absorber and a water impermeable outer sheet. At least a pair of metal layers are placed between the water absorber and the water impermeable outer sheet and extend in the longitudinal direction of the diaper in parallel and one spaced a constant distance from each other. The surface of one of the metal layers is covered with an electrical insulating layer.

The electrostatic capacity, which fluctuates in response to the water content absorbed in the absorber, is detected by applying an alternating current voltage to the metal layers, and the informing means, comprising or oscillator, is activated when the electrostatic capacity exceeds a certain level. An informing signal is transmitted to the receiver located at a remote place and provides the information to the nursing person through alarm signals or the like.

According to the beforementioned structure, the two metal layers, one of which is covered with an electric insulating layer, and the absorber comprises a capacitor, and the electrostatic capacity of this capacitor fluctuates in response to the water content absorbed in the absorber. The degree of wetness of the diaper is determined by the level of the electrostatic capacity. Furthermore, the metal layers are arranged in parallel on the same surface to prevent changes in the distance separating the two layers, as may be caused by patients. In this way, the variation in determining the electrostatic capacity is minimized.

The informing means of the present invention provides convenience to the nurse or nursing person, who is at a remote place such as a nurses' center. The information concerning the wet diaper will be made known through the receiver of the informing system. Therefore, only the wet diaper which needs to be replaced will be changed with a new one in a short time.

The oscillator of the informing means may be of extremely compact size and packed in a waterproof container and connected to the diaper through clip terminals. The oscillator can be removed from the used diaper, so that only the diaper is disposed and the oscillator will be saved for reuse.

A pair of metal layers may be preferably and substantially placed along the center portion of the diaper to minimize mechanical stress and damage to the metal layers. Furthermore, the degree of wetness of the diaper is more precisely detected along the center portion of the diaper.

Other objects, features and advantages of the present invention will become apparent upon perusual of the following detailed description at the preferred embodiments of the present invention when taken in conjunction with the appended drawings.

DETAILED DESCRIPTION OF THE PREFERRED EMBODIMENTS

Figure 1:
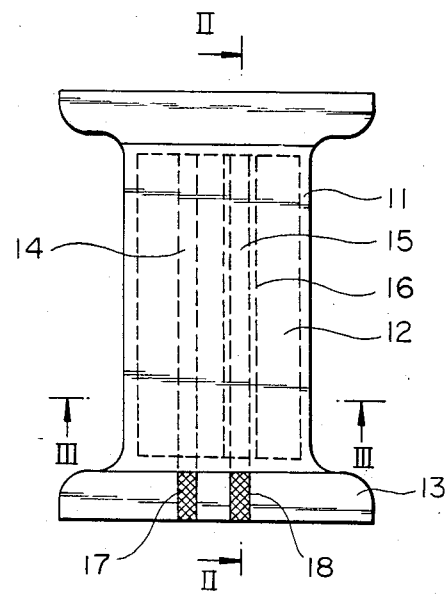
FIG. 1 is a plan view of a disposable diaper with a water content sensing means according to the present invention.

Referring to FIG. 1, a disposable diaper comprised of a water permeable inner sheet 11, a water absorber 12 and a water impermeable outer sheet 13 is shown. The water permeable inner sheet 11 is a non-woven sheet having a texture rate of 10 to 30 g/m$^2$ and is made of rayon, polypropylene or polyester fiber, or a porous and water repelling treated plastic film having a thickness of 50 μm or less. The water absorber 12 is a structural material made of cotton, pulp, tissue paper, super-absorbing polymer, or the like. The outer sheet 13 is a plastic film having a thickness of 30 μm or less and is made of polyethylene, polypropylene, polyester or the like.

Figure 2:
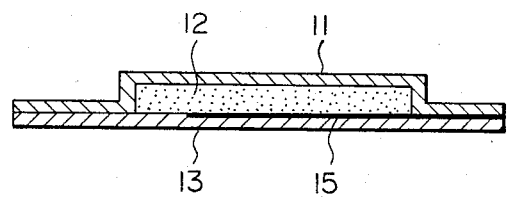
FIG. 2 is a sectional view taken along with the line II—II of FIG. 1.
Figure 3:
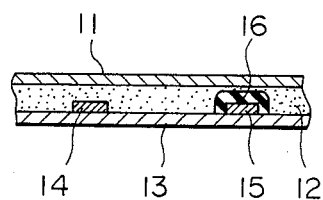
FIG. 3 is an enlarged sectional view taken along with the line III—III of FIG. 1.

As shown in FIGS. 1, 2 and 3, a pair of metal layers 14 and 15 are formed on the outer sheet 13 and they are placed between the outer sheet 13 and the water absorber 12. The metal layers 14 and 15 are formed in a thin layer on the outer sheet 13 by means of lamination or vacuum evaporation of a metallic material such as aluminium, zinc, copper, tin or the like. The pair of metal layers are spaced apart a constant distance and extend in parallel relative to each other in the longitudinal direction of the diaper. One surface of either one of the pair, in the illustrated embodiment the metal layer 15, is covered with an electric insulating layer 16, as shown in FIG. 3. The metal layers 14 and 15 are connected to leads 17 and 18 formed on one end of the outer sheet 13. The leads 17 and 18 are further connected to a device for detecting electrostatic capacity.

Preferably, the metal layers 14 and 15 have a width of 3 mm and a length of at least 50% of the entire length of the diaper. When the metal layers 14 and 15 are formed on the outer sheet 13 by means of lamination, it is preferable to use a metal leaf having a thickness of 5 μm to 15 μm. On the other hand, it is preferable to perform vacuum evaporation under a high vacuum condition of $1 \times 10^{-2}$ Torr or more. The electric insulating layer 16 is formed in a thin layer and has a thickness of 5 μm or less and is made of silicone resin, acryl resin, polyamide resin, nitrile rubber, wax, sodium silicate, polyvinyl alcohol, vinyl acetate or the like.

According to the above mentioned construction, the metal layers 14 and 15 and the electric insulating layer 16 in cooperation with the absorber 12 function as a capacitor when water is absorbed by the absorber 12. The electrostatic capacity of this capacitor varies in accordance with the amount of water absorbed by the water absorber 12. The alternating current voltage is applied to both metal layers 14 and 15 to determine the degree of wetness of the diaper through detection of the variation of the electrostatic capacity. The detecting device is connected to the leads 17 and 18.

To detect the before mentioned electrostatic capacity, it is possible to employ any proper method, such as an AC bridge method, a parallel resonance method, a series resonance method or the like, and those methods are referred to in JIS (Japanese Industrial Standard)-C No. 5102 as typical test methods for the electrostatic capacity for electronic instruments.

Figure 4:
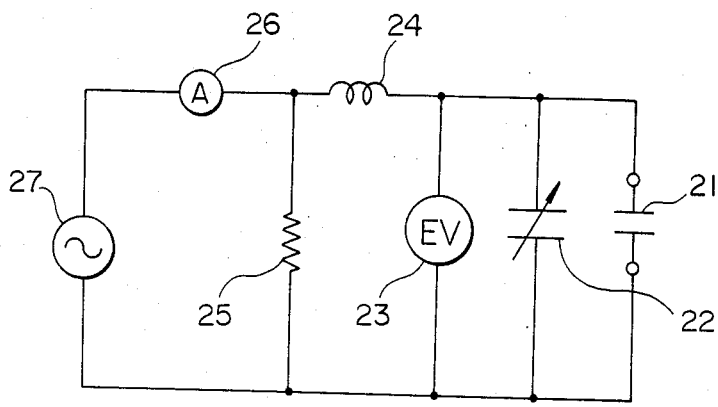
FIG. 4 is a circuit diagram of the detecting device for measuring electrostatic capacity.

In the illustrated embodiment, a measuring circuit according to the series resonance method is shown in FIG. 4. In FIG. 4, numeral 21 is a capacitor having the before mentioned construction and is formed as a diaper. This circuit is further compromised of a variable tuning capacitor 22, an electronic voltage meter 23 having a coil with regulated inductance, a coupling resistance 25, a high frequency ampere meter 26 and AC power source 27.

The procedure for detecting electrostatic capacity (Qx) of capacitor 21 is explained below.

A coil 24 is selected with inductance which corresponds to the frequency of the AC power source 27. The frequency of the AC power source is then adjusted to the prescribed value. Next, the variable tuning capacitor is adjusted to the point Q1 so that the electronic voltage meter indicates the largest value, and the electrostatic capacity C1 of the variable tuning capacitor is read. The capacitor 21 and the variable tuning capacitor 22 are connected in parallel and the variable tuning capacitor 22 is adjusted to the point Q2 which the electronic voltage meter indicates as the largest value. The electrostatic capacity C2 of variable tuning capacitor 22 is then read. The electrostatic capacity of capacitor 21 is obtained by following equation:

$$Qx = C1 - C2 \quad (1)$$

Figure 5:
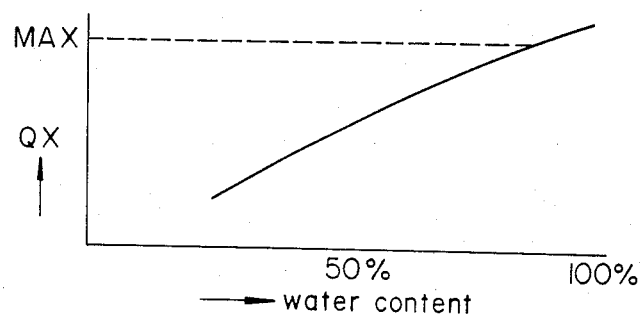
FIG. 5 is a graph illustrating the correlation between water content and electrostatic capacity.

The value of the electrostatic capacity Qx, obtained by the above mentioned manner, varies in accordance with the water content in the water absorber 12. In other words, the value of the electrostatic capacity represents the degree of wetness of the diaper. The correlation between water content (%) and electrostatic capacity is illustrated in the graph of FIG. 5.

For practical application of the above mentioned detecting means, the informing device comprising an oscillator is attached to the detecting circuit and transmits the detected information. A receiver, having an alarm, function, is provided at a remote place, such as a nurse's center to provide the information regarding the condition of the diaper.

Figure 6:
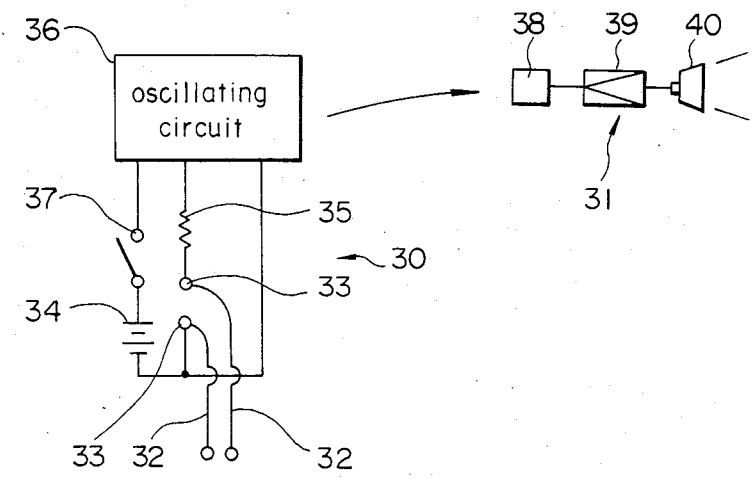
FIG. 6 is a schematic diagram of a modified embodiment of the informing system according to the present invention.
Figure 7:
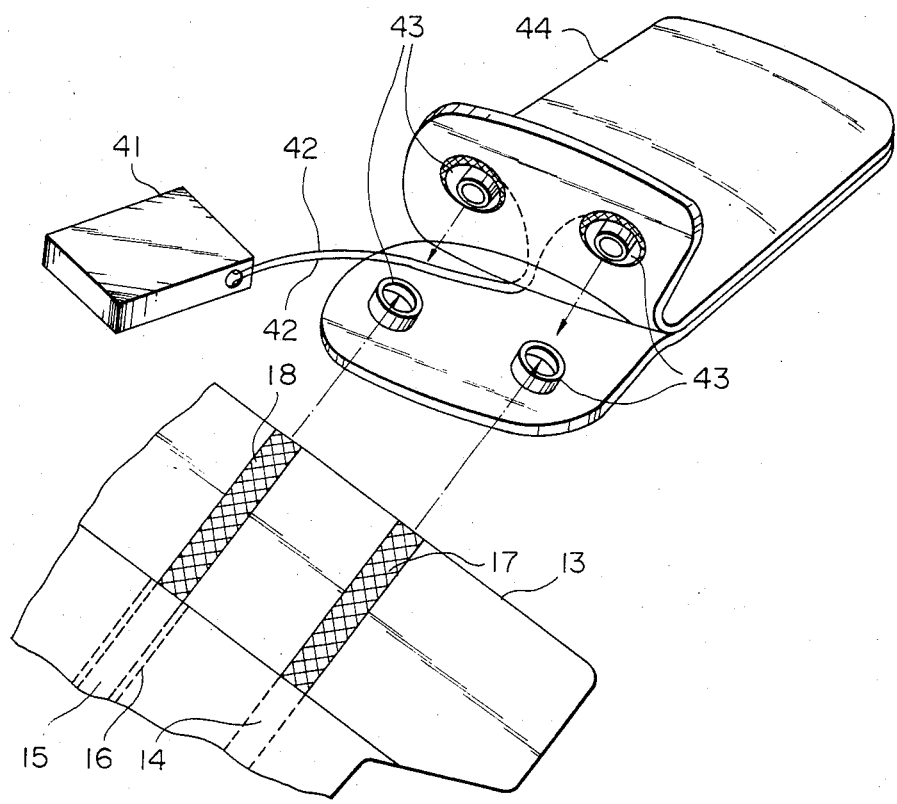
FIG. 7 is a schematic view of the oscillator and its waterproof case with a mounting device for the diaper.
Figure 8:
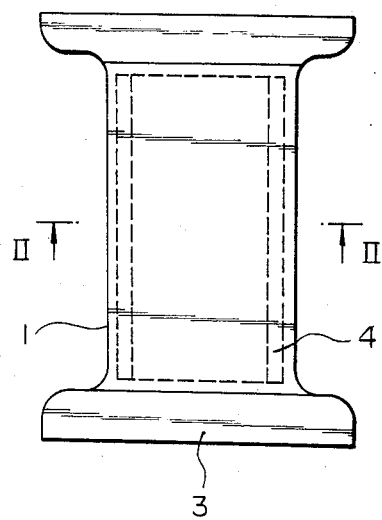
FIG. 8 is a plan view of a prior art water content sensing diaper.
Figure 9:
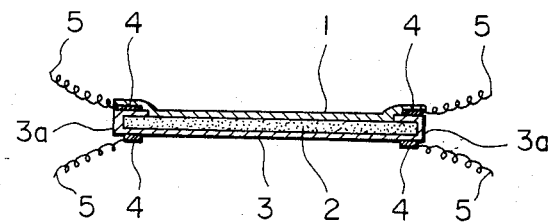
FIG. 9 is a sectional view taken along with the line II—II in FIG. 8.

Referring to FIG. 6 and FIG. 7, a modified embodiment according to the present invention is shown. In the drawings, the same numerals indicate the same or corresponding elements of the before mentioned embodiment, so that the explanation of each element is not repeated. FIG. 6 illustrates an example of an informing system consisting of an oscillator 30 and an alarm device 31. The oscillator 30 comprises input leads 32 connected to the detecting device of FIG. 4, terminals 33, button type cell 34, resistor 35, oscillating circuit 36, and switch 37. The oscillating output of oscillator 30 is transmitted to the receiver 38 of the alarm device which is located at a remote place. The input signal from the oscillator is amplified by amplifier 39 and activates alarm unit 40, which may include a buzzer or a warning lamp.

According to this construction, the output signal is transmitted from the oscillator when the degree of wetness exceeds a certain level indicative of the need to change the diaper.

FIG. 7 illustrates an example of an attaching means for the oscillator 30. The numeral 41 is a box which contains the oscillator 30 and the electrostatic capacity detecting circuit of FIG. 4. The oscillation box 41 has lead wires 42 connected to clip terminals 43 of waterproof case 44. Each clip terminal 43 is comprised of a projecting portion and a recessed portion, which portions engage each other. The leads 17 and 18 formed in the diaper are pressed between the clip terminals 43, so that the metal layers 14 and 15 are electrically connected to the oscillator 30 through the detecting unit.

For practical use, the oscillator box 41 is totally packed in the waterproof case 44, and the case 44 is attached to the diaper through the clip terminals 43. This waterproof case 44 is made of a water-resistant material, such as a synthetic resin or artificial leather. The clip terminals 43 are nickel or chrome plated to resist corrosion. To secure the attachment of the waterproof case 44 and the diaper, the projection or recess may be formed on the clip terminals.

It is preferable to reduce the size of the oscillator and electrostatic capacity detecting unit through IC circuity or the like.

It should be appreciated that, while the various embodiments of the present invention have been described in specific detail, numerous additions, omissions and modifications are possible within the intended spirit and scope of the invention.

What is claimed is:

1. A water content sensing and information system in combination with a disposable diaper comprising a water permeable inner sheet, water absorber, and water impermeable outer sheet, the system comprising:
    at least one pair of metal layers placed between the water absorber and the water impermeable outer sheet, the metal layers spaced a constant distance apart in the same plane, said metal layers extending in the longitudinal direction of the diaper, one surface of one of said metal layers being covered with a layer of electrical insulating material, said electrical insulating material and said absorber being disposed between said metal layers, whereby said metal layers, said insulating material, and said absorber comprise a capacitor;
    a detecting means for determining water content absorbed in the diaper which means applys AC voltage to the metal layers and detects the change of electrostatic capacity of the capacitor and the electrostatic capacity varying depending on the water content absorbed by the absorber; and
    an informing means for informing of the wet condition of the diaper, and the informing means being activated by the output of the detecting means.

2. The water content sensing and informing system according to claim 1, wherein the informing means comprises one of a display device for visually indicating the wet condition of the diaper, and a sound generating device which generates an alarming sound when the detected electrostatic capacity exceeds a prescribed level.

3. The water content sensing and informing system according to claim 2, wherein the informing means comprises an oscillator which is activated by the output of the detecting means and which transmits a signal from the oscillator to a remotely located alarm device, and which alarm device comprises one of the display device and sound generating device and generates alarming information in one of a visual and auditory manner respectively.

4. The water content sensing and informing system according to claim 3, wherein the oscillator and the detecting means are completely packed in a waterproof case which is detachably attached to one end of the diaper.

5. The water content sensing and informing system according to claim 4, wherein the waterproof case comprises a pair of clip terminals provided with corrosion resistance treatment by one of nickel and chrome plating and which are electrically connected to the detecting device, and each terminal consists of a projecting portion and a recessed portion which engage each other so that the case is firmly connected to the leads formed on the diaper.

6. The water content sensing and informing system according to claim 1, wherein the metal layers are formed in a thin layer on the water impermeable outer sheet by means of lamination or vacuum evaporation of a metal and have a thickness of 5 $\mu$m to 15 $\mu$m, which metal is selected from the group aluminium, zinc, copper and tin.

7. The water content sensing and informing system according to claim 6, wherein the metal layers are electrically connected to the detecting means through leads formed at one end of the diaper.

8. The water content sensing and informing system according to claim 1, wherein the metal layers are formed substantially in the center portion of the diaper.

9. A wetness indicator system for use with a disposable diaper having a water permeable inner sheet and a water impermeable outer sheet, comprising:
(a) capacitor means comprising first and second coplanar, parallel metal means, one surface of one of said metal means being covered with an electrical insulating material, and a water absorber disposed between said metal means and said electrical insulating material, said capacitor means for being positioned between the water permeable and the water impermeable sheets, said capacitor means having an electrostatic capacity proportional to the amount of water absorbed by said water absorber;
(b) detector means associated with said capacitor means for detecting changes in the electrostatic capacity of said capacitor means; and,
(c) informing means operably associated with said detector means for indicating the degree of wetness of said water absorber.

10. The system of claim 9, wherein:
(a) said detector means including means for applying a voltage to said metal means.

11. The system of claim 9, wherein:
(a) said informing means including an alarm means; and,
(b) said detector means including means for activating said alarm means when the electrostatic capacity of said capacitor means exceeds a preselected level.

12. The system of claim 11, wherein:
(a) said alarm means being located remote from said capacitor means; and,
(b) said informing means including an oscillator transmitting a signal to said alarm means for causing operation of said alarm means and said oscillator being activated by said detector means.

13. The system of claim 9, wherein:
(a) said metal means each comprising a metallic layer having a thickness of from between about 5 $\mu$m to about 15 $\mu$m; and, (b) said metallic layers each comprised of a metal selected from the group of aluminium, zinc, copper and tin.

14. The system of claim 9, wherein:
(a) means detachably connecting said detector means to said metal means.

15. A wetness indicating diaper, comprising:
(a) a water permeable inner sheet;
(b) a water absorber overlayed by said inner sheet;
(c) a water, impermeable outer sheet overlayed by said water absorber;
(d) a pair of uniformly spaced apart coplanar metal layers disposed on said outer sheet and engaged with said water absorber and at least one of said metal layers having a surface thereof covered with an electrical insulating layer and said electrical insulating layer and said absorber being disposed between said metal layers and thereby providing a capacitor having an electrostatic capacity varying in response to the water absorbed by said absorber;
(e) detector means connected to said metal layers for monitoring the electrostatic capacity of said capacitor; and,
(f) means associated with said detector means for indicating the wetness of said absorber.

16. The diaper of claim 15, wherein:
(a) said detector means including means for applying a voltage to said layers;
(b) said indicating means including an oscillator for transmitting an alarm signal; and,
(c) an alarm device being located remote from said indicating means and being activated by the alarm signal.

17. The diaper of claim 16, wherein:
(a) means detachably connecting said detector means to said layers.

18. The diaper of claim 17, wherein:
(a) said detector and indicating means being positioned in a waterproof container.

19. The diaper of claim 16, wherein:
(a) said metal layers each being comprised of a material selected from the group aluminum, zinc, copper and tin.

* * * * *